United States Patent [19]

Ruppert

[11] Patent Number: 5,152,775
[45] Date of Patent: Oct. 6, 1992

[54] AUTOMATIC LANCET DEVICE AND METHOD OF USING THE SAME

[76] Inventor: Norbert Ruppert, 1501 Lexington Ave., Deland, Fla. 32724

[21] Appl. No.: 592,842

[22] Filed: Oct. 4, 1990

[51] Int. Cl.$^5$ ............................................. A61B 17/32
[52] U.S. Cl. .................................... 606/182; 221/270; 221/271
[58] Field of Search ................ 606/182, 183, 181, 185, 606/189; 604/62; 206/366; 221/232, 238, 270, 271; 128/637

[56] References Cited

U.S. PATENT DOCUMENTS

| | | | |
|---|---|---|---|
| D. 297,978 | 10/1988 | White | D24/28 |
| 2,632,444 | 3/1953 | Kas | 604/62 |
| 3,030,959 | 4/1962 | Grunert | 606/182 |
| 4,230,118 | 10/1980 | Holman et al. | 128/314 |
| 4,388,925 | 6/1983 | Burns | 128/314 |
| 4,445,510 | 5/1984 | Rigby | 128/329 R |
| 4,449,529 | 5/1984 | Burns et al. | 128/314 |
| 4,527,561 | 7/1985 | Burns | 128/314 |
| 4,535,769 | 8/1985 | Burns | 128/314 |
| 4,539,988 | 9/1985 | Shirley et al. | 128/314 |
| 4,553,541 | 11/1985 | Burns | 128/314 |
| 4,616,649 | 10/1986 | Burns | 128/314 |
| 4,624,253 | 11/1986 | Burns | 128/314 |
| 4,658,821 | 4/1987 | Chiodo et al. | 128/314 |
| 4,677,979 | 7/1987 | Burns | 128/314 |
| 4,715,374 | 12/1987 | Maggio | 128/314 |
| 4,844,095 | 7/1989 | Chiodo et al. | 128/314 |
| 4,856,515 | 8/1989 | Turner et al. | 128/315 |

FOREIGN PATENT DOCUMENTS

| | | | |
|---|---|---|---|
| 2131297 | 1/1973 | Fed. Rep. of Germany | 606/182 |
| 1065689 | 5/1954 | France | 606/181 |

*Primary Examiner*—Michael H. Thaler

[57] ABSTRACT

An automatic lancet apparatus stores a plurality of sterile lancet needles which are loaded one at a time into an injecting position. After use of a needle, the apparatus ejects the used needle prior to loading a fresh needle. The needles include a cover over their tip ends which is automatically removed during loading. The loading operation also serves to reset the apparatus in preparation for injection. Once the needles are placed in the storage chamber, they are loaded, used, and ejected without further handling.

8 Claims, 2 Drawing Sheets

AUTOMATIC LANCET DEVICE AND METHOD OF USING THE SAME

This invention relates to automatic lancet devices and, more particularly, to lancet devices in which a plurality of needles stored in the device and the device is operable to automatically load a new needle and discard a used needle at each operation.

BACKGROUND OF THE INVENTION

Numerous automatic lancet devices have been developed having a lancet needle on the free end of a movable arm which is urged by a spring force from a retracted, cocked position to an operating position in which the needle pricks a person's finger to yield a blood sample. The known prior art devices have a single needle which is manually loaded into the device and manually removed after use. In some devices, it is anticipated that the needle will be cleaned by application of alcohol and used for other patients. Because of recent concerns about transmission of disease through blood testing, it has become desirable to assure that lancet needles are not reused. It is further desirable that the automatic lancet device be one which can be rapidly loaded and unloaded in order to accommodate multiple patients. It is further desirable that the lancet device minimize the opportunity for the user of the device to be pricked by the lancet needle during loading and unloading of the device.

SUMMARY OF THE INVENTION

The above and other desirable features are attained in an automatic lancet device including a housing which holds a plurality of lancet needles. In one form of the invention, the lancet needles are arranged so as to be spring urged into a loading position. A slide member has a first slot which can be aligned with one of the needles and can transport one of the needles at a time into an injecting position. The slide member is preferably arranged to cam operate an injecting device so that motion of the slide member causes the device to be cocked into an injecting position. The needle transported by the slide member is captured in a receiving means in an injecting station. The slide member is then moved to an intermediate position whereby a second slot in the slide member overlays the needle in the injecting position. The device may be then actuated by depression of a trigger to release the receiving means under spring force to cause the needle to be impelled into the finger of a patient. The needle is then removed from the receiving means by moving the slide member to a second intermediate position in which the used needle in the second slot becomes free to fall from the lancet device. The slide member can then be moved back to its first extreme position to pick up another needle for use. In a preferred form, the needles are grouped into a continuous strip by intermediate plastic elements and the needles are themselves encased in plastic housings. A plastic cover extends over the tip of each needle so as to prevent injury to a person loading needles into the housing. The device includes apparatus for automatically stripping the covering from the tip ends of the needles as the slide member transports the needles to the injecting position. The lancet device of the present invention may also include means for receiving a platform having a beveled aperture adapted for positioning of a finger therein. The aperture is aligned with the needle when the needle is in its injecting position. The platform assures uniform penetration of the needle a preselected distance into the finger. The housing may also include a continuous strip of flexible material on a roll which can be pulled over the platform after each use to provide a degree of protection between the finger of one patient and that of another. The continuous strip may be advanced after each use in order to provide a fresh surface for each subsequent user.

BRIEF DESCRIPTION OF THE DRAWINGS

For a better understanding of the present invention, reference may be had to the following detailed description taken in conjunction with the accompanying drawings in which.

DETAILED DESCRIPTION OF THE INVENTION

Figure 1A:
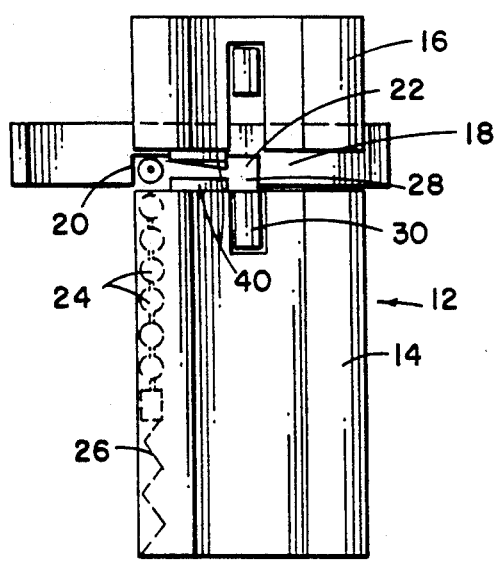
FIGS. 1A, 1B, and 1C are front elevation views of an automatic lancet apparatus in accordance with the present invention.
Figure 1B:
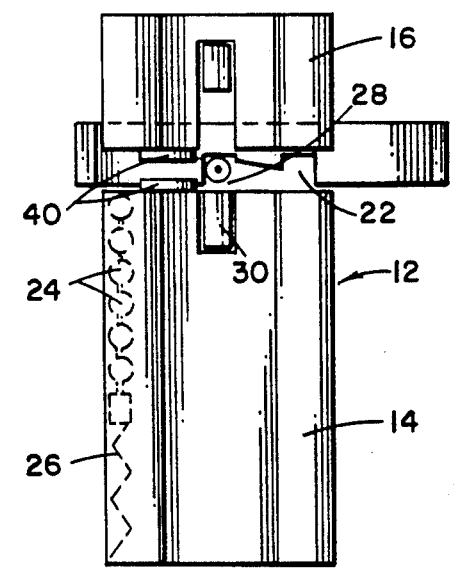
Figure 1C:
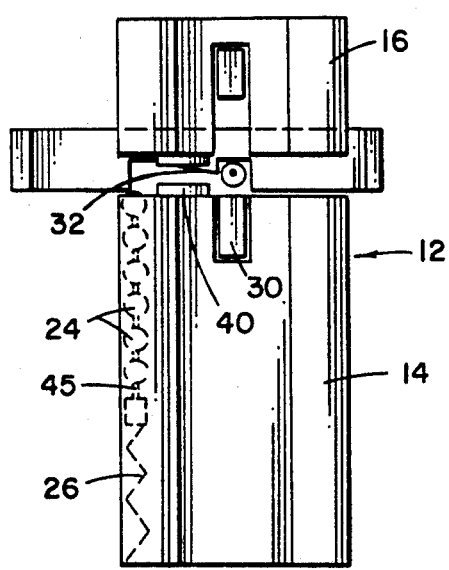

Referring first to FIGS. 1A, 1B, and 1C, there is shown a simplified elevation view of a front end of an automatic lancet device in accordance with the teaching of the present invention. The device comprises a casing 12 preferably formed of plastic or other lightweight material and having a lower portion 14 and an upper portion 16. Between the lower portion 14 and the upper portion 16, there is provided a spacing in which there is positioned a slide member 18. The slide member 18 includes a first slot 20 and a second parallel slot 22. A plurality of lancet needles 24 is stored within the housing 12. Spring device 26 biases the needles upward toward the slide member 18.

Figure 2:
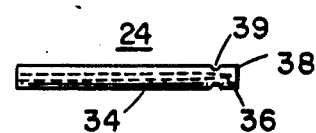
FIG. 2 is an elevation view of a lancet needle for use with the lancet apparatus of FIG. 1A.

In the operation of the illustrative device, as the needles 24 are biased upward, one of the needles enters the slot 20, FIG. 1A, where it is captured by the slide member 18. The slide member 18 is thereafter moved to the right hand direction into the position shown in FIG. 1B to transport one of the needles 24 into the location indicated at 28. In this injecting location, the needle is captured by an injecting device 30. In order to utilize the needle in the injecting position 28, the slide member 18 must be moved to the position indicated in FIG. 1C. In so doing, the slide member rides upward over the needle in the injecting position by means of the inclined plane 32 formed on the slide member between the slots 20 and 22. The slide member 18 is moved to the left until the slot 22 overlays the needle in the position 28. In this position, the needle can be driven forward, i.e., in a direction out of the plane of the paper, in order to puncture a finger of a person whose blood is to be tested. Once the needle has been used, the slide member 18 is again moved towards the right hand edge into the position shown in FIG. 1B such that the used needle captured in the slot 22 is pushed laterally out of the injecting position. By tipping the device towards its front surface after pushing slide 18 to the position of FIG. 1B, the used needle can be caused to simply fall out of the slot 22 and thereby be disposed of. The slide 18 can then be moved back to the position of FIG. 1A to capture a new needle in the slot 20 for transport into the injecting position 28 so that the device is again ready to be used. Referring briefly to FIG. 2, there is shown a side view of one of the needles 24. The needle is captured in a plastic needle holder 34 and has a tip end 36 enclosed within a plastic cover 38. A small notch 39 separates holder 34 from cover 38 and is defined by a reduced thickness of plastic which is easily removed. When the needles 24 are transported from the loading position at the extreme left side of the device, the plastic portion 38 is automatically separated by an element 40 located on the lower portion of the case 14. The method of separation will become apparent from the description of the figures to follow.

It will be appreciated from the above description of operation that a used needle is ejected before a fresh needle can be loaded. This process assures sterility of the needles and prevents the protective cover 38 of the fresh needle from being removed before the used needle is ejected. The slide 18 is spring loaded to return to the position of FIG. 1C when a needle is positioned in the injecting location. The spring action is chosen so as to prevent the slide 18 from pushing the needle to the left side, i.e., the spring is sufficiently weak that it cannot force the needle out of the injecting position. As will become apparent, the needle is held tightly in the injecting position so as to require manual force to remove it.

Figure 3:
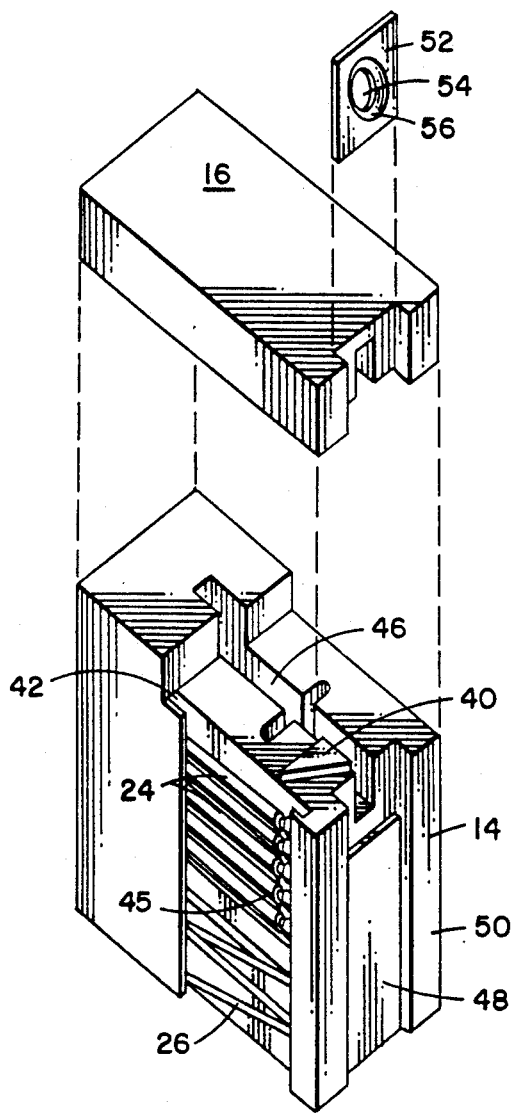
FIG. 3 is an exploded perspective view of a portion of the lancet apparatus of FIG. 1A.

Turning now to FIG. 3, there is shown a simplified partial perspective view of the lancet device of FIG. 1 with the upper section 16 removed from the lower section 14 and with the slide member 18 and injection device 30 omitted. In this view, it can be seen that the needles 24 are positioned within a slot 42 on the side of the case 12. Spring means 26 biases the needles 24 upwardly until it contacts with the slide member 18. The needles are preferably held together in a continuous chain of needles by means of a flexible plastic member 45 (shown oversized for clarity) which is easily severed as the needles are picked up by the slide member 18. The lower section 14 and upper section 16 have mating slots 46 within which the injection device 30 slides. The element 40 which removes the plastic cover 38 from the needle tip ends 36 is shown as a triangular member attached to the upper surface of case portion 14. A mating triangular section is also preferably formed on a lower surface of the upper section 16 to assist in pulling the covers 38 from the needles. When one of the needles 24 is picked up by the slide member 18 and the slide member is moved laterally to transfer the needle to the injecting position, the needle tip is forced past the triangular member 40 which fits into the slot or spacing 39 between the needle cover 34 and the tip cover 38. As the needle is moved from left to right across the device 12, the triangular portion separates the cover 38 from the needle and forces it to be discarded out the front of the device 12. Thus, when the needle is in the injecting position within the injecting device 30, the cover 38 has been removed from the needle and the tip of the needle is exposed.

FIG. 3 also shows a slot 48 running vertically up the front face 50 of the housing 12. The upper portion of the slot 48 is sized to accept a platform 52. The platform 52 is provided with a center aperture 54 and a tapered bowl-like depression 56 leading to the aperture 54. The platform 52 provides a convenient place for positioning a person's finger at the front of the device 12 in preparation for puncturing the finger with one of the needles 24. The lower portion of the slot 48 is not as deep as the upper portion which receives the platform 52. The remainder of the slot 48 is designed to pass a flexible strip of material which can be pulled through the slot and overlay the platform 52 to provide a degree of isolation between the platform 52 and a person's finger. The strip may be pulled up and overlay the platform for each person to be examined. After a person's finger is punctured, the strip may be pulled upward to present a new section to the platform 52 and allow a used section to be torn off and discarded.

Figure 7:
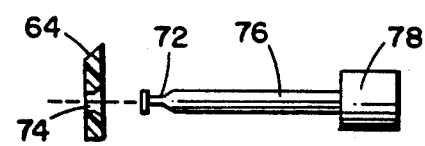
FIG. 7 is an elevation view of the release and trigger mechanism of FIG. 4.
Figure 4:
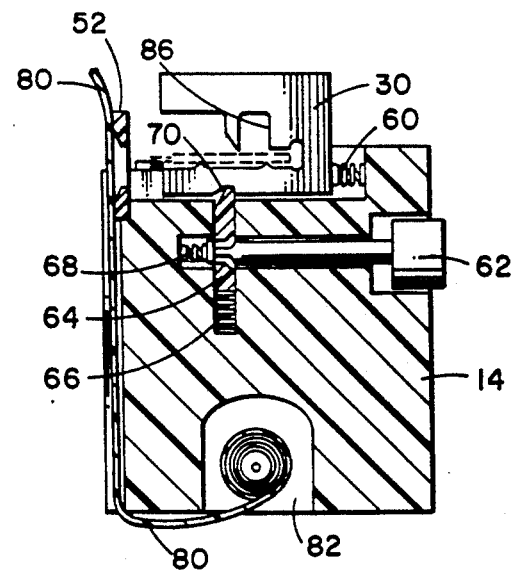
FIG. 4 is a cross-sectional view taken through the slot 46 of the lancet apparatus of FIG. 3.
Figure 5:
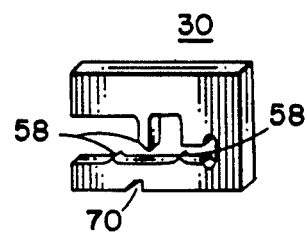
FIG. 5 is a perspective view of the device 30 of FIG. 4.

Referring now to FIG. 4, there is shown a cross-sectional view taken through the slot 46 of FIG. 3. In this figure, the upper section 16 has been omitted and the injection device 30 included. The injection device 30 is designed to capture and hold one of the needles 24 using opposed teeth 58. Referring briefly to FIG. 5, there is shown a perspective view of an injection device 30. The teeth 58 are relatively sharp and are designed to puncture the plastic material encompassing the needle Referring again to FIG. 4, the injection device is propelled forward by spring 60 compressed between a portion of the lower housing 14 and the device 30. The device 30 is held in a cocked position by means of a trigger mechanism including a trigger 62 and a release 64. A spring 66 biases the release 64 towards the member 30 while a spring 68 biases the trigger 62 into a ready position. When the trigger 62 is pressed inward, the release 64 is forced downward retracting it from a notch 70 in the device 30 and allowing the device 30 to be propelled forward. As can be seen, the trigger 62 has a relatively narrow portion 72 which fits through an aperture 74 (see FIG. 7) in the release 64. A larger diameter shaft section 76 connects a head 78 of the trigger to the narrow portion 72. The connection between the shaft section 76 and the narrow portion 72 is provided by a tapered segment which operates against a tapered entry into the aperture 74 and release 64 in a manner to force the release member 64 in a downward direction in order to center the aperture 74 on the shaft portion 76.

FIG. 4 also illustrates the use of a roll of continuous flexible material 80 positioned within an aperture 82 in the lower portion of the casing 14. The strip material is pulled off of the roll and fed through the slot 48 along the face 50 of the device 12. The material extends upward and overlays the platform 52.

Figure 6:
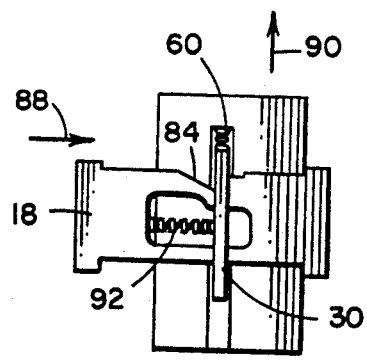
FIG. 6 is a top plan view of the lancet apparatus of FIG. 1A with top portion 16 removed.

As was previously stated, the slide member 18 functions not only to transport the needles from the loading position and into the injecting device 30 but also serves to position the device 30 in its cocked position in preparation for use of one of the needles 24. Referring now to FIG. 6, there is shown a top view of the device 12 with the upper housing section 16 removed. The slide member 18 can be seen to have a cam section 84 which operates against a surface 86 (see FIG. 4) on member 30. As the slide member 18 is moved in the direction indicated by the arrow 88, the cam surface 84 operates against the surface 86 to force the injector device 30 in the direction indicated by arrow 90. As the member 30 is pushed in the indicated direction, it reaches a point at which the release 64 can be pushed into the slot 70 thereby retaining the member 30 in the cocked position. It will be noted that the lancet device cannot be fired until the slide member 18 has been returned to the position indicated in FIG. 6. This is the position shown in the illustration of FIG. 1C. The spring 92 drives the member 18 to this position.

In the operation of the illustrated automatic lancet device, the needles 24 are loaded into the slot 42 on the side of the housing section 14. The slide member is then moved to its extreme left hand position (FIG. 1A) in order to place the slot 20 over the needles and enable one of the needles to enter into the slot. The slide member is then moved to its extreme right hand position (FIG. 1B) in order to transport the needle 24 to the injecting position within the injecting device 30. The slide member is then moved to the left again (FIG. 1C) such that the slot 22 overlays the needle in the injecting position. When the trigger 62 is depressed, the release 64 is forced downward thereby releasing the injecting mechanism 30 so that the spring 60 pushes the mechanism 30 forward to cause the needle tip 36 to project through the aperture 54 within the platform 52. If the strip material 80 is being used, a person's finger will have depressed the strip material against the aperture 54 so that the needle will puncture both the strip material and the person's finger. After use, the slide member 18 is again moved towards the right hand position in order to transport the used needle out of the injecting position and allow it to be discarded by falling out of the front of the device. When it is desired to use the device again, the slide member 18 is pushed fully to the left hand position of FIG. 1A and a fresh needle is transported into the injecting device while the cover 38 is removed from the needle by the stripping mechanism 40 during such transport. Because the slide member 18 which serves to transport needles between the storage position, the injection position, and the discarding position is also utilized to effect cocking of the injecting mechanism, it will be appreciated that the device cannot be cocked and reused until a used needle has been removed from the injecting position and into a discarding position.

While the invention has been described in what is presently considered to be a preferred embodiment, many modifications and variations will become apparent to those skilled in the art. It is intended therefore that the invention not be limited to the disclosed embodiment but be interpreted within the full spirit and scope of the appended claims.

What is claimed is:

1. A method of operating an automatic lancet device having a housing and a plurality of needles stored in the housing, a slide member operative transversely of a direction of injection of the needles for transporting the needles from storage to an injecting position, the slide member having a pair of spaced slots for picking up and discarding needles, a spring actuated needle injector and a trigger for actuating the injector, the method comprising the steps of:

(a) moving the slide member to a first extreme position to pick up one of the needles in the first slot;
(b) sliding the slide member to a second extreme position for transporting the one of the needles to the injecting position;
(c) sliding the slide member to an intermediate position whereby the second slot is oriented with the one of the needles in the injecting position;
(d) actuating the trigger to cause the one of the needles to be thrust forward a preselected distance;

(e) moving the slide member toward the second extreme position to remove the one of the needles from the injecting position and tilting the housing to allow the one of the needles to be discarded; and
(f) repeating the steps (a) through (e) for each subsequent operation of the lancet device.

2. A lancet device comprising:
a housing;
means for storing a plurality of disposable lancet needles in said housing;
means for selectively advancing one of said needles into an operative position to be driven a preselected distance out of said housing;
actuating means operable to drive said one of said needles out of said housing said preselected distance;
means for transporting and for ejecting said one of said needles out of said housing and for inhibiting operation of said actuating means until said one of said needles is ejected;
means coupled to said transporting means for resetting said actuating means in preparation for advancing another of said needles into said operative position; and
said needles being spring biased toward said advancing means and said advancing means comprising a slide member operative generally perpendicular to a direction in which said needles are driven and having a first slot sized to accept a single one of said needles, sliding motion to said slide member in a first direction being operative to transfer one of said needles from a loading position to said operative position.

3. The lancet device of claim 2 wherein said actuating means comprises a spring driven needle receiving means and a trigger mechanism for holding said receiving means in a cocked position pending actuation of said trigger mechanism.

4. The lancet device of claim 3 wherein said slide member is operative to force said receiving means into said cocked position during transport of a needle into and out of said receiving means.

5. The lancet device of claim 4 and including a removable platform coupled to said housing and positioned in an aligned orientation with said one of said needles in said operative position, said platform including a depression with a center aperture for passage of a point of said one of said needles upon actuation of said actuating means.

6. The lancet device of claim 5 and including a continuous strip of flexible material mounted on a roll coupled to said housing, a slot being formed in said housing for passing said strip in an overlaying position with respect to said platform.

7. The lancet device of claim 2 wherein said slide member includes a second slot spaced from said first slot, one side of said first slot having a tapered edge whereby sliding motion of said slide member in a second direction opposite to motion in said first direction causes said slide member to ride over said one of said needles until said one of said needles is positioned in said second slot.

8. The lancet device of claim 7 wherein each of said needles includes a protective cover over a tip end thereof, and means coupled to said housing for removing said cover during transport of each of said needles into said operative position.

* * * * *